United States Patent [19]
Tanaka

[11] Patent Number: 5,417,216
[45] Date of Patent: May 23, 1995

[54] MECHANICAL RADIAL SCAN TYPE ULTRASOUND PROBE

[75] Inventor: Toshizumi Tanaka, Omiya, Japan

[73] Assignee: Fuji Photo Optical Co., Ltd., Omiya, Japan

[21] Appl. No.: 282,737

[22] Filed: Jul. 29, 1994

[30] Foreign Application Priority Data

Jul. 29, 1993 [JP] Japan ................................. 5-205591

[51] Int. Cl.⁶ ............................................... A61B 8/12
[52] U.S. Cl. ............................ 128/660.10; 128/662.06
[58] Field of Search ...................... 128/660.08, 660.09, 128/660.10, 662.06; 73/633, 634

[56] References Cited
U.S. PATENT DOCUMENTS 4,732,156  3/1988  Nakamura .................. 128/660.09

*Primary Examiner*—George Manuel
*Attorney, Agent, or Firm*—Oblon, Spivak, McClelland, Maier, & Neustadt

[57] ABSTRACT

A mechanical radial scan type ultrasound probe which essentially includes: a tubular probe body having an ultrasound transducer element mounted at the fore end of a rotation transmission means; an operating unit accommodating a rotational drive means for driving a rotational shaft, and an angular position detector means for detecting angular positions of the rotational shaft; and a forcibly releasable joint means interposed between the rotation transmission means and the rotational shaft in association with forcibly turning means, the forcibly releasable joint means being arranged to couple the rotation transmission means securely with the rotational shaft to follow the rotation of the latter under normal condition and to permit relative rotations of the rotation transmission means and the rotational shaft when the forcibly turning means is manipulated with a force larger than the coupling force of the releasable joint means, for shifting the angular position of the ultrasound transducer element relative to an initial end position of radial scan field.

5 Claims, 4 Drawing Sheets

MECHANICAL RADIAL SCAN TYPE ULTRASOUND PROBE

BACKGROUND OF THE INVENTION

1. Field of the Art

This invention relates to a mechanical radial scan type ultrasound probe with an ultrasound transducer element to be rotated within an intracorporeal or intracavitary portion for examination or diagnostic purposes.

2. Prior Art

Ultrasound diagnosis systems which are currently in use for medical examinations are often equipped with the so-called mechanical radial, scan type ultrasound probes which are designed to be inserted into an intracavitary portion of human body. The ultrasound probes of this sort have an ultrasound transducer element connected to a rotational drive means thereby to put the ultrasound transducer element in rotation while transmitting ultrasound pulses into an intracavitary wall portion of interest at predetermined angular intervals and receiving return echoes for stratigraphic images of intracavitary wall tissues. The return echo signals thus received by the ultrasound transducer element are sent to a signal processor in a control section of an ultrasound image observation unit to form video signals of an ultrasound picture image through predetermined signal processing operations for display on a monitor.

In mechanical radial scan operations, one frame of ultrasound picture image is obtained on each revolution of the ultrasound transducer element, starting from a preset initial scan position. Namely, ultrasound picture signals for one frame of ultrasound image are produced as the ultrasound transducer element is turned through 360° from a predetermined initial scan position, and the single-frame ultrasound picture signals are converted into video signals to display a video image on a monitor screen. For this purpose, the signal processor includes a scan converter with a memory for storing the ultrasound echo signals, which are received through the ultrasound transducer element, along with angular position signals from an angular position detection means which detects rotational angles of the ultrasound transducer element. The stored echo signals are converted into video signals as they are read out from the memory.

In a radial ultrasound scanning operation, an ultrasound image is displayed by means of a large number of acoustic lines which are arranged radially and successively at predetermined angular intervals through 360° from a scan initiating end position corresponding to a predetermined original position on the monitor screen. These acoustic lines correspond to the ultrasound echo signals which are sampled at predetermined time intervals along the time axis. Therefore, although the time differential between two adjacently adjoining acoustic lines is ignorably small, it gradually increases to bring about an appreciable discrepancy between the acoustic lines at the initial and terminal end positions of the 360° scan field. More specifically, since an intracavitary organ under examination is usually in motion, an appreciably large time differential makes it difficult to match the ultrasound image segments of the initial and terminal acoustic lines which are sampled in different phases in time. Namely, it causes a discontinuity in ultrasound picture image across the initial and terminal acoustic lines of the 360° scan field. Such a discontinuity in picture image could occur to a region of special interest, making it difficult for the operator to go into a close examination of that region. Of course, the initial scan position of the ultrasound probe relative to a particular intracavitary region can be adjusted by changing the position of the ultrasound probe itself. within an intracavitary portion. However, such re-positioning of the entire body of the inserted ultrasound probe could result in unexpectedly large deviations of the ultrasound transducer element from an intracavitary portion of interest.

SUMMARY OF THE INVENTION

With the foregoing situations in view, the present invention has as its object the provision of a mechanical radial scan type ultrasound probe which can adjust the scan initiating end position of the probe arbitrarily without entailing re-positioning of the ultrasound probe as a whole within an inserted intracavitary portion.

It is a more specific object of the present invention to provide a mechanical radial scan type ultrasound probe which permits to remove a discontinuity or discrepancy in ultrasound image between acoustic lines at scan initiating and terminating ends of radial scan field away from or clear of a particular locality of an intracavitary region under examination by the ultrasound probe.

In accordance with the present invention, the above-stated objectives are achieved by the provision of a mechanical radial scan type ultrasound probe which essentially includes: a tubular probe body having an ultrasound transducer element mounted at the fore end of a rotation transmission means; an operating unit accommodating a rotational drive means for driving a rotational shaft, and an angular position detector means for detecting angular positions of the rotational shaft; and a forcibly releasable joint means interposed between the rotation transmission means and the rotational shaft in association with forcibly turning means, the forcibly releasable joint means being arranged to couple the rotation transmission means securely with the rotational shaft to follow the rotation thereof under normal condition and to permit relative rotations of the rotation transmission means and the rotational shaft when the forcibly turning means is manipulated with a force larger than the coupling force of the releasable joint means, for shifting the angular position of the ultrasound transducer element relative to an initial end position of radial scan field determined on the basis of a position signal from the angular position detector means.

BRIEF DESCRIPTION OF THE DRAWINGS

The above and other objects, features and advantage of the present invention will become apparent from the following description and the appended claims, taken in conjunction with the accompanying drawings, which show by way of example a preferred embodiment of the invention and in which:

DESCRIPTION OF PREFERRED EMBODIMENTS

Figure 1:
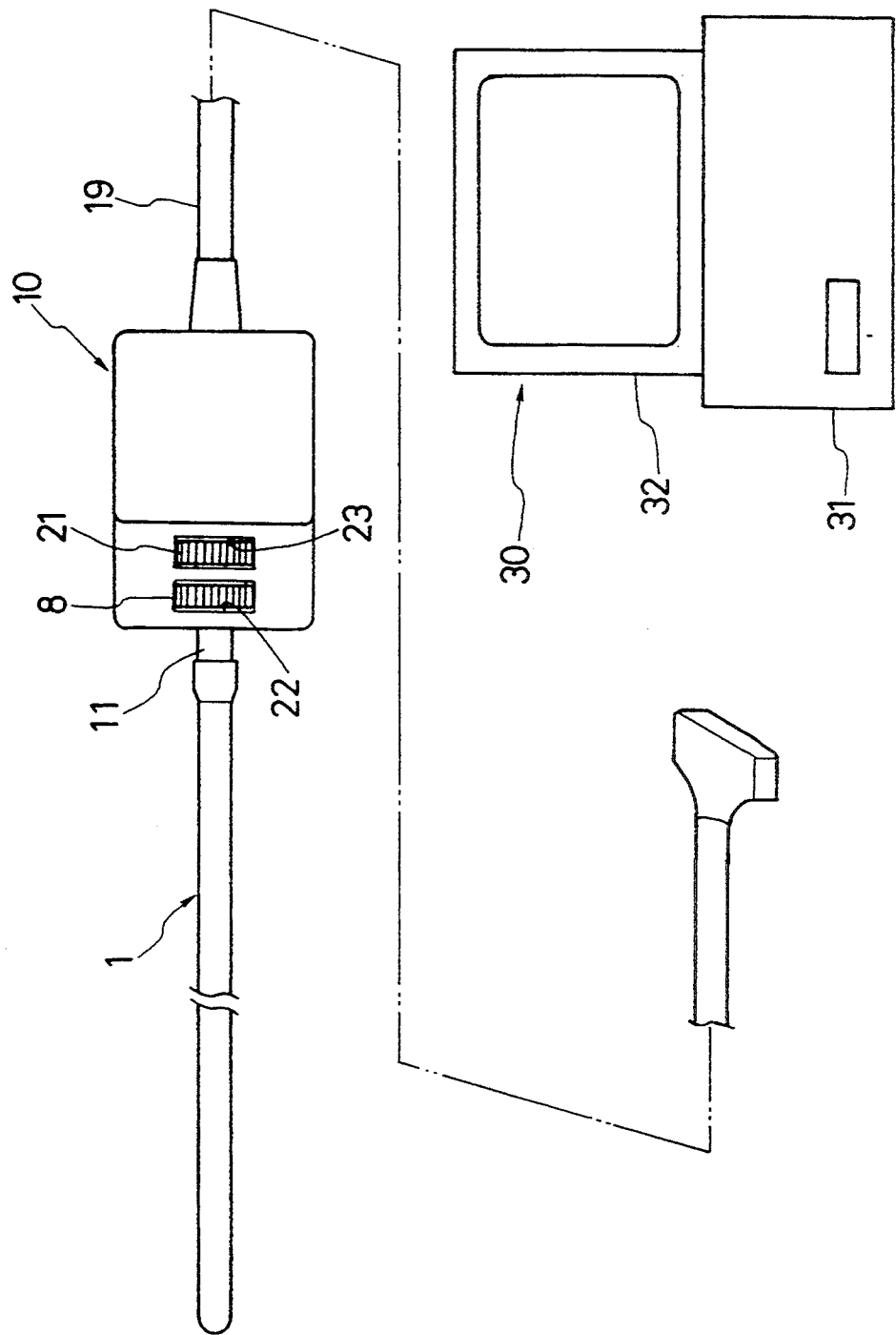
FIG. 1 is a schematic illustration of general configuration of an ultrasound examination system with a mechanical radial scan type ultrasound probe according to the invention.

Hereafter, the invention is described more particularly by way of a preferred embodiment shown in the drawings.

Figure 2:
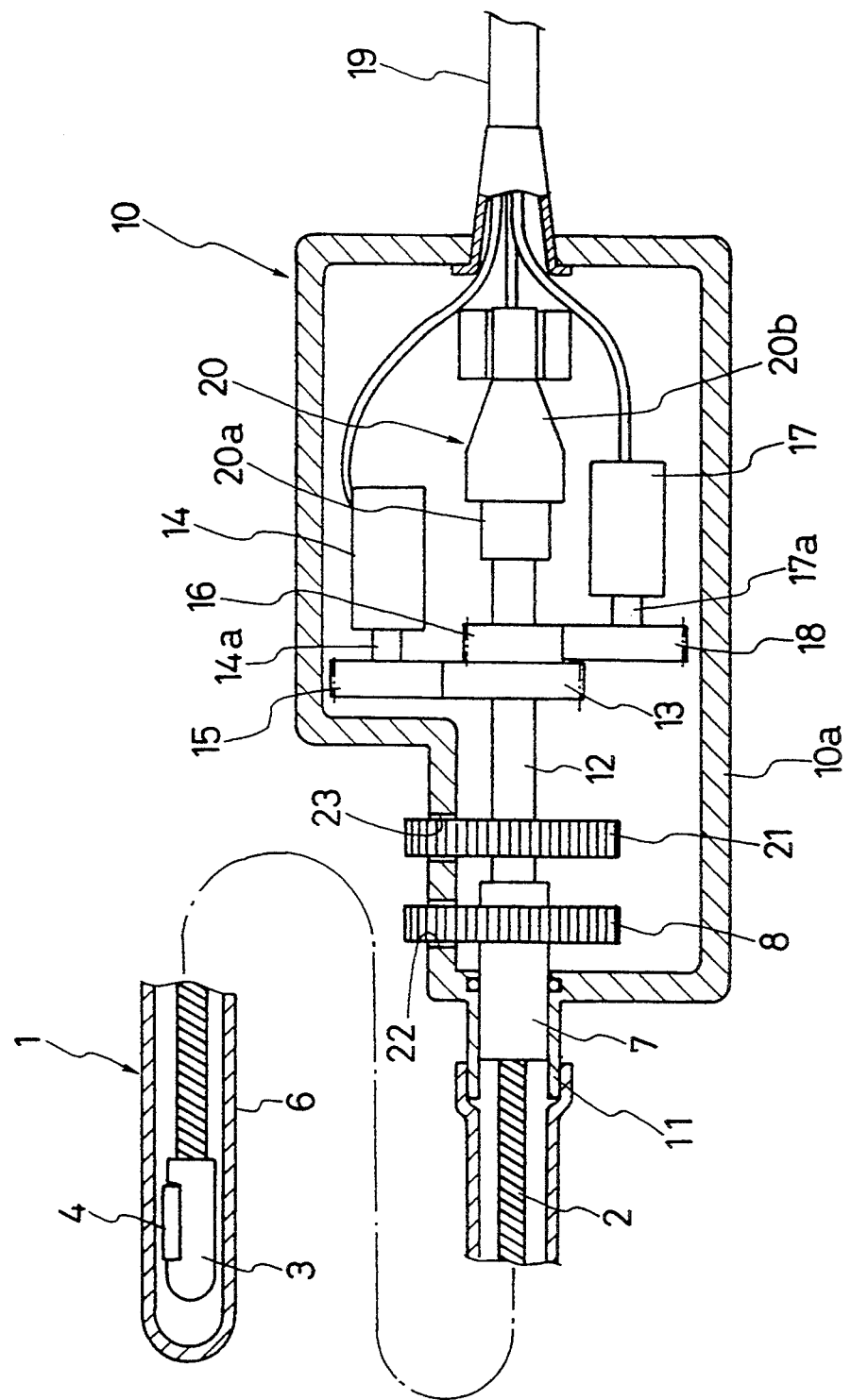
FIG. 2 is schematic sectional view of the ultrasound probe and an operating unit.
Figure 3:
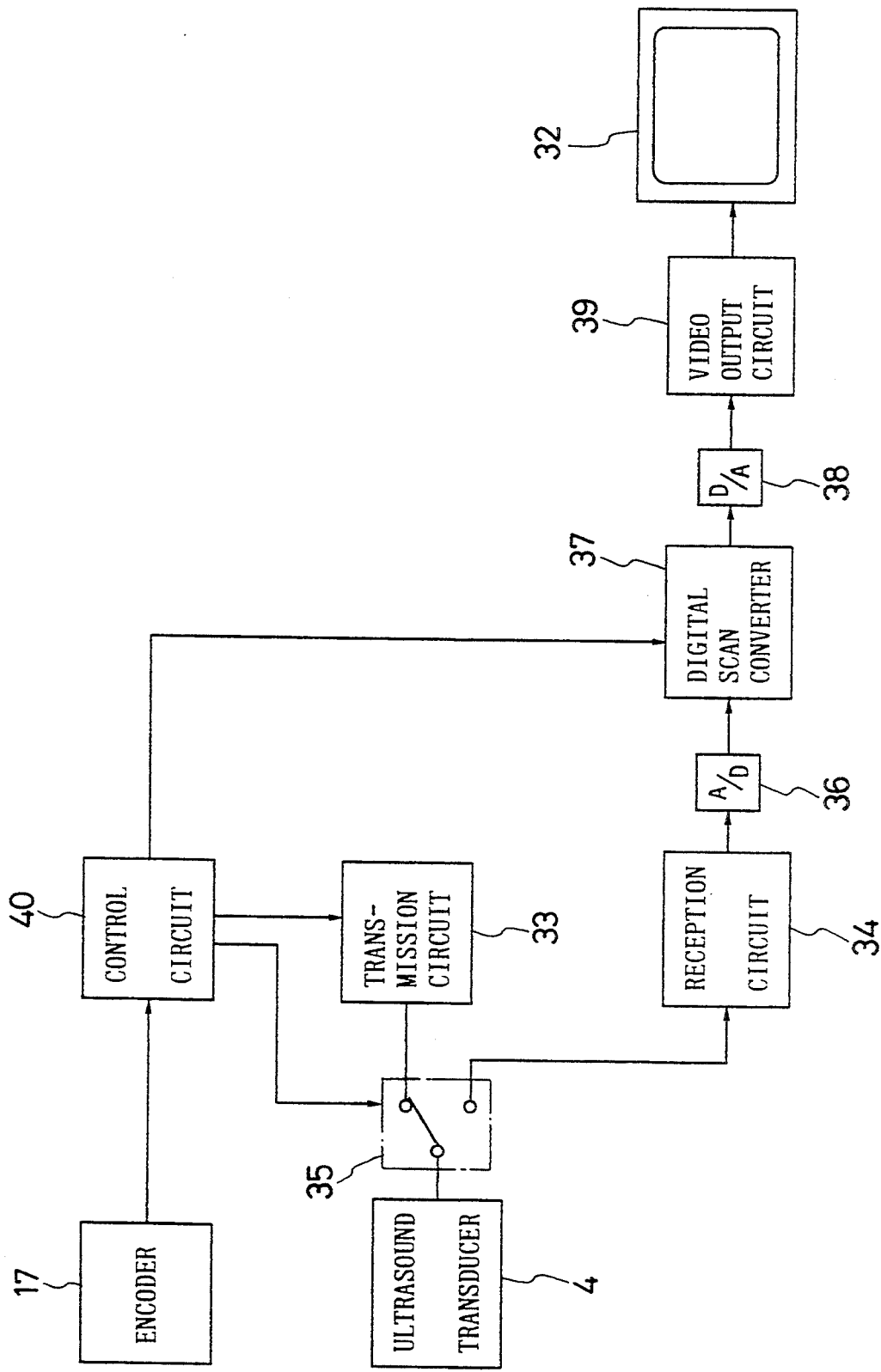
FIG. 3 is a circuit diagram of a controller for the ultrasound examination system.

Illustrated in FIG. 1 is the general configuration of an ultrasound examination system, including a mechanical radial scan type ultrasound probe and an operating unit, which are shown more particularly by the sectional view of FIG. 2. This ultrasound examination system is not an external examination type which percutaneously transmits ultrasound pulses to examine organs or tissues under the skin but a direct insertion type having an ultrasound probe to be inserted directly into an intracavitary portion closely in face to face relation with a region of interest to be scanned for examination or for diagnostic purposes.

Figure 5:
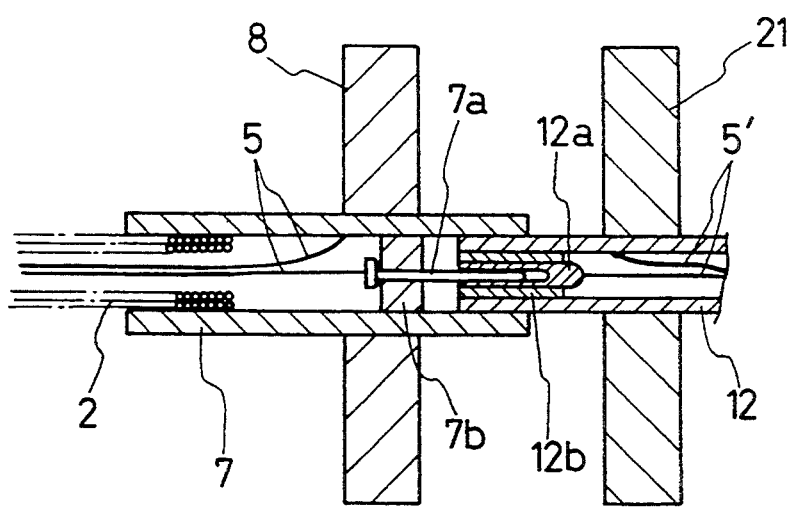
FIG. 5 is a sectional view of a forcibly releasable joint provided between the ultrasound probe and the operating unit.

In FIG. 1, indicated at 1 and 10 are the above-mentioned ultrasound probe proper and the operating unit, which are connected to an ultrasound image observation unit 30. The ultrasound probe 1 is tailored into a form which is suitable for insertion into intracavitary portions of human body through a guide means such as a biopsy channel which is usually provided on an endoscope for insertion of forceps or other instruments. In this regard, the ultrasound probe 1 is provided with a rotation transmission shaft 2 of a length and a thickness suitable for this purpose. Attached to the fore end of the rotation transmission shaft 2 is a rigid tip member 3 which supports thereon an ultrasound transducer element 4. The rotation transmission shaft 2 is preferred to be flexible and to be capable of transmitting rotation accurately, and in this particular embodiment, it is constituted by a number of coiled metal wires which are wound in parallel relation with each other or in multiple layers, forming a hollow space in a center portion to receive a signal cable or wiring 5 (FIG. 5). Since the ultrasound probe 1 is intended to be directly inserted into an intracavitary portion as mentioned hereinbefore, it is preferred to be as small as possible in diameter including its fore end portion containing the tip member 3 with a rigid structure. Accordingly, the tip member 3 should be extremely small in size, not to mention the ultrasound transducer 4 which is normally in the form of a single-element transducer.

The tip member 3 is provided with a rigid structure suitable for supporting the ultrasound transducer element 4, and, together with the rotation transmission cable 2, encased in a sleeve 6 of a synthetic resin material which has excellent acoustic properties and which is closed at the fore end, so that rotation is smoothly transmitted to the tip member 3 when the rotation transmission shaft 2 is turned about its axis in radial scan operations, free of possibilities of intracavitary wall portions being caught by the tip member 3 which is put in rotation for radial scans. The interior of the sleeve 6 is filled with an ultrasound transmission medium, for example, a liquid with excellent acoustic and lubricative properties. The sleeve 6 has its base end portion fixedly fitted on a connector portion 11 on a casing 10a of the operating unit 10.

On the other hand, the rotation transmission shaft 2 has its base end connected to a coupling member 7 which is rotatably received in the connector portion 11 and extended into the casing 10a. The coupling member 7 is fittingly coupled with a rotational shaft 12 which is rotatably supported within the casing 10a of the operating unit 10. Mounted on the rotational shaft 12 is a driven gear 13 which is held in meshing engagement with a drive gear 15 on the output shaft 14a of a motor 14. Therefore, as the motor 14 is actuated, its rotation is transmitted to the rotational shaft 12 through the intermeshed drive and driven gears 15 and 13 and then to the rotation transmission shaft 2 through the coupling member 7, thereby rotationally driving the ultrasound transducer element 4 on the tip member 3 at the fore distal end of the rotation transmission shaft 2 by remote control. Also mounted on the rotational shaft 12 is a second gear 16 which is meshed with a follower gear 18, which follower gear 18 is in turn connected to an input shaft 17a of a rotary type encoder 17. This encoder 17 serves to detect the angular position of the ultrasound transducer element 4 and is constituted by, for example, an incremental encoder with a Z-phase indicative of the original position of radial scan.

The coupling member 7 and the rotational shaft 12 are coupled with each other through a joint which transmits rotation of the rotational shaft 12 securely to the coupling member 7 when the former is driven from the motor 14 under normal condition. More specifically, the coupling member 7 which is slidably received in the connector portion 11 is connected to the rotation transmission cable 2 which is in turn connected at its fore end to the ultrasound transducer element 4. The rotation of the ultrasound transducer element 4 is met by a certain degree of resistance as it is rotated within the sleeve 6 together with the rotation transmission shaft 2. In this particular embodiment, the joint between the coupling member 7 and the rotational shaft 12 is arranged to hold them with a frictional coupling force which can well overcome the resistances which may exist in the path of transmission of rotation from the rotational shaft 12 to the ultrasound transducer element 4. Therefore, when the rotational shaft 12 is put in rotation by the motor 14, its rotation is transmitted securely to the ultrasound transducer element 4 free of slips or similar troubles at the joint portion. However, as will be described hereinlater, the frictional joint between the coupling member 7 and the rotational shaft 12 is forcibly releasable against the frictional coupling force to permit their relative rotations upon application of an external force which is greater than the frictional coupling force.

The wiring lines 5 which are connected to the ultrasound transducer element 4 are passed through the rotation transmission shaft 2 and connected to corresponding wiring lines 5' on the part of the operating unit 10 through the coupling member 7 and the rotational shaft 12. The wiring lines 5' on the operating unit 10 are bundled together with wirings for the motor 14 and the encoder 17 to form a cable 19 which is led out of the casing 10a of the operating unit 10. The other remote end of the cable 19 is detachably connected to the ultrasound image observation unit 30 in an non-rotatable state. Therefore, a rotary connector 20 is connected between the rotational shaft 12 and the cable 19. The rotary connector 20 is composed of a rotatable member 20a and a fixed member 20b in a manner well known in the art, which are connected to the rotational shaft 12 and the cable 19, respectively. The rotatable member 20a and fixed member 20b are electrically connected with each other through conductive brush or fluid contact.

The ultrasound image observation unit 30 is constituted by a controller 31 and a monitor device 32. The controller 31 is connected to the operating unit 10 and the ultrasound transducer element 4 through the cable 19 to supply power to the motor 14 and to apply transmission and reception trigger signals to the ultrasound transducer element 4. Further, return echo signals received by the ultrasound transducer element 4 are fed to the controller 31 together with output signals of the encoder 17 indicative of angular positions of the transducer element 4. The return echo signals are processed into video signals in a known manner to display an ultrasound image of the scanned portion on the monitor 32. The controller 31 is therefore provided with a signal transmission circuit 33 and a signal reception circuit 34 which are alternately connectible to the ultrasound transducer element 4 through a switch 35. The signal reception circuit 34 is connected to a digital scan converter 37 through A/D converter 36. The signals from the ultrasound transducer element 4 are fed to the digital scan converter 37 and stored in its memory. The stored signals of ultrasound image are read out frame by frame from the memory of the digital scan converter 37, and converted into video signals of a format suitable for display on the monitor 32, supplying the video signals to the monitor 32 through D/A converter 38 and picture signal output circuit 39. Further, the controller 31 is provided with a control circuit 40 which controls the timing of ultrasound pulse generation by the signal transmission circuit 33 in relation with the switching operation by the switch 35 and the write-in and read-out operations by the digital scan converter 37. The control circuit 40 is arranged to control the respective components according to the position signals of the ultrasound transducer element 4, which are supplied from the encoder 17.

With the above-described arrangements according to the present invention, after inserting the ultrasound probe 1 into an intracavitary portion of interest, the motor 14 is actuated to put the ultrasound transducer element 4 in rotation and simultaneously transmission trigger signals are fed thereto from the signal transmission circuit 33 to release ultrasound pulses into the intracavitary portion from the transducer element 4 at predetermined angular intervals. The ultrasound transducer element 4 is alternately connected to the signal reception circuit 34 by the switch 35 to receive return echo signals from the scanned sectional areas of the intracavitary portion, the received echo signals being sent to the signal reception circuit 34 and stored in the memory of the digital scan converter 37 together with the position signals from the encoder 17 indicative of angular positions of the ultrasound transducer element 4. In this manner, signals of the respective acoustic lines are stored in the digital scan converter 37. As soon as the memory is filled with 360° picture data or one frame picture data, they are read out from the digital scan converter 37, followed by conversion into video signals suitable for display on the monitor 32.

Figure 4:
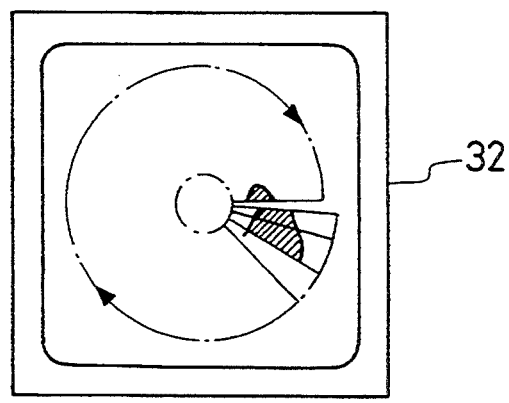
FIG. 4 is a diagrammatic illustration explanatory of a discontinuity in a radial ultrasound image displayed on a monitor screen.

In this instance, when the ultrasound transducer element 4 is put in rotation for a radial scan operation, there invariably exists a time differential between the individual ultrasound signals which are sampled at predetermined angular positions to make up one frame of ultrasound picture image. Namely, the time differential occurs to each of the acoustic lines which follow the acoustic line at the initial position of 360° radial scan field. Therefore, when sampling data sequentially along the time axis through 360° from the initial to terminal end position of the radial scan field, the time differential between the adjacently adjoining acoustic lines is substantially ignorably small in value, but it accumulates and amounts to a considerably large value toward the terminal end position of 360° radial scan field, often resulting in a discontinuity in ultrasound image across the terminal and initial end positions. Such a discontinuity in ultrasound image renders close examinations impossible particularly when the image of an intracavitary portion of interest lies across the terminal and initial end positions as indicated by hatching in FIG. 4.

The initial end position of radial scan is set by an original position signal based on a Z-phase of the encoder 17, irrespective of the actual position of the ultrasound transducer element 4 at the time of starting its rotation. At the start of a radial scan, if the ultrasound transducer element 4 is located in a position away from the original position as set by the encoder 17, it is turned into the initial end position of the encoder by a pre-rotation. Upon detecting location of the ultrasound transducer. element 4 at the initial .end position of the radial scan field, the control circuit starts sampling of ultrasound echo signals, supplying the return echo signals to the digital scan converter 37. In this regard, the above-described forcibly releasable joint according to the present invention is provided with simple and inexpensive means for varying the direction of the ultrasound transducer element 4 relative to the original position of the encoder arbitrarily for the purpose of shifting a discontinuity in ultrasound picture image, which might occur to the initial end position of the radial scan field, away from an intracavitary portion of particular interest.

More specifically, the coupling member 7 and the rotational shaft 12 are connected to forcibly rotating members 8 and 21 in the form of rings, respectively, which can be forcibly turned by manual operation. These forcibly rotating members 8 and 21 are partly exposed to the outside through openings 22 and 23 which are formed in the casing 10a. As described hereinbefore, under normal condition, the joint between the coupling member 7 and the rotational shaft 12 is arranged to transmit the rotation of the rotational shaft 12, driven by the motor 14, accurately to the coupling member 7 to let the ultrasound transducer element 4 follow its rotation in a secure manner. For this purpose, the coupling member 7 and the rotational shaft 12 are fittingly joined with each other to provide a frictional coupling which is strong enough to overcome various resistive forces which might exist in the path of transmission of rotation from the rotational shaft 12 to the tip member 3. However, the forcibly releasable joint permits relative rotations of the coupling member 7 and the rotational shaft 12 when the forcibly rotating members 8 and 21 are turned with a force which is stronger than the frictional coupling force of the joint.

A forced relative rotation can be attained, for example, by forcibly turning the rotating member 21 with a finger while holding the other rotating member 8 against rotation with other finger or fingers, or alternatively by turning the two forcibly rotating members 8 and 21 in opposite directions. By so doing, the rotational shaft 21 is turned through a certain angle together with the second gear 16 which is in meshed engagement with the follower gear 18 on the input shaft 17a of the encoder 17, shifting the angular position of Z-phase of the encoder 17 which determines its original position of radial scan in the rotational direction. As a result, the angular position of the scan initiating end of the ultrasound transducer element 4 is shifted in a substantial degree to remove a discontinuity in ultrasound image across the terminal and initial ends of the radial scan field to a position remote from an image of an intracavitary portion which needs a closer examination. This makes it possible to eliminate undetectable regions in ultrasonically scanned areas almost completely in mechanical radial scan operations.

The wiring lines 5 for the ultrasound transducer element 4 are connected to corresponding wiring lines 5' on the side of the rotational shaft 12 through the coupling member 5 and the rotational shaft 12 which are relatively rotatably joined with each other as described above. Shown in FIG. 5 an arrangement for making electric connections between the relatively rotatable coupling member 7 and rotational shaft 12.

The coupling member 7 is in the form of a cylinder of rigid conductive material and internally provided with an electrode pin 7a. The electrode pin 7a is anchored in an insulating member 7b and protruded out of the base end of the coupling member 7 over a predetermined length. On the other hand, the rotational shaft 12 is also in the form of a cylinder of rigid conductive material, with a socket member 12a fixedly fitted therein through an insulating member 12b. As the coupling member 7 is fittingly engaged with the rotational shaft 12, a signal line of the wiring 5 of the ultrasound transducer element 4 is electrically connected to the socket member 12a through the electrode pin 7a, while an earth line of the wiring 5 is electrically connected to the rotational shaft 12 through the coupling member 7, permitting relative rotations of the coupling member 7 and rotational shaft 12 by the provision of the electrode pin 7a and the socket member 12a. More specifically, With this joint construction, relative angular positions of the coupling member 7 and the rotational shaft 12 can be varied by a relative forced rotation through manipulation of the rotating members 8 and 21, without breaking electrical connections between the wirings 5 and 5' and free of possibilities of forcibly breaking the wirings 5 and 5' themselves by relative rotations of the coupling member 7 and rotational shaft 12.

If the rotational shaft 12 is put in rotation by the motor 14 after adjusting the position of the scan initiating end in the above-described manner, the rotation is securely transmitted to the coupling member 7 by the large frictional coupling force at the joint of the rotational shaft 12 and the coupling member 7. Accordingly, the turning force is securely transmitted through the rotation transmission shaft 2 down to the ultrasound transducer element 4 on the tip member 3 at the fore end of the rotation transmission shaft 2, without causing deviations of the position signals produced by the encoder 17 on rotation of the rotational shaft 12 from actual angular positions of the ultrasound transducer element 4.

What is claimed is:

1. A mechanical radial scan type ultrasound probe, comprising:
    a tubular probe body having an ultrasound transducer element mounted at the fore end of a rotation transmission means;
    an operating unit accommodating a rotational drive means for driving a rotational shaft, and an angular position detector means for detecting angular positions of said rotational shaft; and
    a forcibly releasable joint means interposed between said rotation transmission means and said rotational shaft in association with forcibly turning means, said forcibly releasable joint means being arranged to couple said rotation transmission means securely with the rotational shaft to follow the rotation of the latter under normal condition and to permit relative rotations of said rotation transmission means and said rotational shaft when said forcibly turning means is manipulated with a force larger than the coupling force of the releasable joint means, for shifting the angular position of said ultrasound transducer element relative to an initial end position of radial scan field.

2. A mechanical radial scan type ultrasound probe as defined in claim 1, wherein said initial end position of radial scan field is determined by an original scan position signal of a rotary type encoder mounted on said operating unit in association with said rotational shaft.

3. A mechanical radial scan type ultrasound probe as defined in claim 1, wherein said forcibly releasable joint is arranged to join said rotation transmission means and said rotational shaft together with a frictional coupling force, and has a ring-like forcibly rotating member connected to said rotational shaft to permit relative rotations of said rotation transmission means said forcibly rotating members is manually operated against the frictional coupling force of said joint.

4. A mechanical radial scan type ultrasound probe as defined in claim 3, wherein said rotation transmission means is in the form a rotation transmission shaft consisting of a large number of tightly wound wire coils, and joined with said rotational shaft through a cylindrical coupling member frictionally in engagement with said rotational shaft, said coupling member being caused to slip on said rotational shaft when applied with an external force greater than said frictional coupling force of said joint.

5. A mechanical radial scan type ultrasound probe as defined in claim 4, wherein said coupling member is formed of conductive material, and said rotational shaft is in the form of a hollow cylinder of conductive material, and wherein said joint is arranged to connect signal lines of wiring for said ultrasound transducer element through relatively rotatable connector members mounted on said coupling member and rotational shaft while connecting earth lines through joined bodies of said coupling member and rotational shaft.

* * * * *